US006498268B1

(12) United States Patent
Raths

(10) Patent No.: US 6,498,268 B1
(45) Date of Patent: Dec. 24, 2002

(54) METHOD FOR PRODUCING ALKYLENE GLYCOL ESTERS WITH LIMITED HOMOLOGUE DISTRIBUTION

(75) Inventor: Hans-Christian Raths, Monheim (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/486,401
(22) PCT Filed: Aug. 17, 1998
(86) PCT No.: PCT/EP98/05204
§ 371 (c)(1),
(2), (4) Date: May 19, 2000
(87) PCT Pub. No.: WO99/10309
PCT Pub. Date: Mar. 4, 1999

(30) Foreign Application Priority Data

Aug. 25, 1997 (DE) .......................... 197 36 906
Sep. 25, 1997 (DE) .......................... 197 41 911
Feb. 23, 1998 (DE) .......................... 198 07 597

(51) Int. Cl.⁷ .............................. C07C 67/26
(52) U.S. Cl. ........................ 560/200; 560/209
(58) Field of Search ................. 560/209, 200

(56) References Cited

U.S. PATENT DOCUMENTS

| 3,884,946 A | 5/1975 | Sung et al. |
| 4,557,846 A | 12/1985 | Wisotsky |
| 4,609,376 A | 9/1986 | Craig et al. |
| 4,684,473 A | 8/1987 | Bock et al. |
| 4,885,008 A | 12/1989 | Ishizaki et al. |
| 5,936,107 A | * 8/1999 | Raths et al. ............ 554/149 |

FOREIGN PATENT DOCUMENTS

| DE | 20 24 050 A | 12/1971 |
| DE | 35 34 442 A1 | 4/1987 |
| DE | 37 21 119 | 1/1989 |
| DE | 37 38 812 | 5/1989 |
| EP | 0 178 913 | 4/1986 |
| EP | 0 608 149 A1 | 7/1994 |
| WO | WO 98/25878 | 6/1998 |

OTHER PUBLICATIONS

Bartholome, et al., "Ullman's Encyklopädie der technischen Chemie", Band 4, Verlag Chemie, Weinheim (1976), p.540.
Behr, et al., Fat Sci. Technol., 93, (1991), pp. 340–345.
Spiteller, Fat Sci. Technol., 94, (1992), pp. 41–46.
Daute, et al., Fat Sci. Technol., 95, (1993), pp. 91–94.
Otter, Fette, Seifen, Anstrichmittel (Fats, Soaps, Coatings), 72, (1970), p. 667.

* cited by examiner

Primary Examiner—Mukund J. Shah
Assistant Examiner—Zachary C. Tucker
(74) Attorney, Agent, or Firm—John E. Drach; Aaron R. Ettelman

(57) ABSTRACT

A method of producing alkylene glycol esters of unbranched aliphatic dicarboxylic acids with limited homolog distribution, and the use of the esters produced as monomer structural units for producing polymers are disclosed.

11 Claims, No Drawings

METHOD FOR PRODUCING ALKYLENE GLYCOL ESTERS WITH LIMITED HOMOLOGUE DISTRIBUTION

CROSS-REFERENCE TO RELATED APPLICATIONS

This application is a 35 U.S.C. §371 national stage application based upon International Application No. EP98/05204, filed on Aug. 17, 1998.

BACKGROUND OF THE INVENTION

This invention relates to a process for the production of so-called narrow-range alkylene glycol esters of unbranched aliphatic dicarboxylic acids and to their use as a monomer unit for the production of polymers.

The addition of alkylene oxides onto CH-acid compounds such as, for example, fatty alcohols, alkyl phenols, fatty amines or even fatty acids is one of the industrially established processes for the production of nonionic surfactants. These reactions are normally carried out in the presence of homogeneous basic catalysts such as, for example, sodium hydroxide or sodium methylate. Unfortunately, alkoxylation lacks selectivity as a reaction with the result that, in practice, it is found that the maximum of the resulting homolog distribution does not correspond with the average degree of alkoxylation, particularly with low alkoxylation ratios.

Attempts have been made to counteract this unwanted effect by using catalysts which have greater selectivity and which, overall, lead to alkoxylates, particularly ethoxylates, with a narrow homolog distribution. These products are often also referred to in the literature as "narrow-range ethoxylates". Preferred homogeneous catalysts for this purpose are alkaline earth metal salts, for example barium phosphate or strontium ether carboxylates. Heterogeneous catalysts, for example calcined hydrotalcites, ay also be used for this purpose.

However, known processes for ethoxylating fatty acids have failed to produce satisfactory results. In particular, attempts to produce fatty acids with low degrees of ethoxylation, particularly fatty acid+1EO adducts, which are of interest as intermediates for the synthesis of ether sulfate surfactants with an isethionate-like structure, have revealed unsatisfactory selectivities. Besides the unwanted presence of homologs with relatively high degrees of ethoxylation, significant amounts of polyethylene glycol and diesters in particular are also formed. The process according to U.S. Pat. No. 3,884,946 (Henkel), which recommends using amines as catalysts for this purpose, also provides the "low-ethoxylated" fatty acids in yields well below 90% of the theoretical.

According to EP-A-178 913, not only straight-chain fatty acids, but also branched neocarboxylic acids with a tertiary carbon atom adjacent the carboxyl group can be alkoxylated with high selectivity in the presence of amines, such as diethanolamine and triethanolamine. However, if high yields are to be obtained by this process, relatively high temperatures of 140 to 185° C. have to be applied.

According to the cited prior art, the problem of the selectivity of the alkoxylation process has only been investigated for monomeric carboxylic acids. However, the problem of selective alkoxylation has not hitherto been addressed or, according to EP-A-178 913, has only been tentatively addressed for oligomeric carboxylic acids, more particularly unbranched aliphatic dicarboxylic acids. Accordingly, there is a need to find a selective process for the alkoxylation of unbranched aliphatic dicarboxylic acids.

BRIEF SUMMARY OF THE INVENTION

Accordingly, the problem addressed by the present invention was to provide an improved process for the production of alkylene glycol esters of unbranched aliphatic dicarboxylic acids, more particularly unbranched aliphatic dicarboxylic acids with low degrees of alkoxylation, using a homogeneous catalyst which would be distinguished by improved selectivity.

Surprisingly, the problem stated above has been solved by the use of alkanolamines, particularly triethanolamine, as catalyst in the addition of alkylene oxides onto the unbranched aliphatic dicarboxylic acids. This process is particularly suitable for the production of unbranched aliphatic dicarboxylic acids with low degrees of alkoxylation.

Accordingly, the present invention relates to a process for the production of alkylene glycol esters of unbranched aliphatic dicarboxylic acids by addition of alkylene oxides onto unbranched aliphatic dicarboxylic acids in the presence of basic catalysts, characterized in that alkanol-amines are used as the basic catalysts.

In the context of the present invention, the expressions "alkoxylated unbranched aliphatic dicarboxylic acids" and "alkylene glycol esters of unbranched aliphatic dicarboxylic acids" are used synonymously. The expressions "addition of alkylene oxides" and "alkoxylation" are also used synonymously.

DETAILED DESCRIPTION OF THE INVENTION

Dicarboxylic Acids

In the context of the present invention, unbranched aliphatic dicarboxylic acids are those which have no branches in the hydrocarbon group. Unbranched aliphatic $\alpha,\omega$-dicarboxylic acids corresponding to formula (I):

$$\text{HOOC—R—COOH} \tag{I}$$

in which R is a difunctional, unbranched, aliphatic, saturated and/or unsaturated hydrocarbon group, are preferred. The substituent R is preferably a hydrocarbon group of the described type containing 1 to 20 carbon atoms. Suitable dicarboxylic acids for the purposes of the invention are malonic acid, succinic acid, adipic acid and azelaic acid, which are commercially obtainable, and the unbranched aliphatic $\alpha,\omega$-dicarboxylic acids which can be obtained by fermentative or microbial processes from alkanes, alkenes, alcohols or esters thereof in the presence of a microorganism of the genus *Candida tropicalis* in the presence of nutrients and optionally co-substrates in accordance with DE-A-37 21 119 or DE-A-37 38 812. Unbranched $\alpha,\omega$-aliphatic dicarboxylic acids containing 10 to 20 hydrocarbon groups (R in formula (I)), which may even unsaturated, can be obtained particularly easily by this process.

According to the invention, unbranched aliphatic $\alpha,\omega$-dicarboxylic acids selected from the group consisting of malonic acid, succinic acid, adipic acid and azelaic acid are preferred.

Alkanolamines

Typical examples of alkanolamines, which may be used as homogeneous basic catalysts, are monoethanolamine, diethanolamine and preferably triethanolamine. The alkanolamines are normally used in quantities of 0.05 to 5% by weight and preferably in quantities of 0.1 to 1.5% by weight, based on the dicarboxylic acids.

Alkoxylation

The alkoxylation may be carried out by methods known per se and is described in the following with reference by way of example to ethoxylation.

Normally, the unbranched aliphatic dicarboxylic acid and the catalyst are first introduced into a stirred autoclave which is freed from traces of water before the reaction by alternate evacuation, preferably at temperatures of 80 to 120° C., and purging with nitrogen. The unbranched aliphatic dicarboxylic acid is then reacted with the ethylene oxide which may be introduced into the autoclave in portions via a siphon after heating.

The molar reaction ratio of unbranched aliphatic dicarboxylic acid to ethylene oxide is preferably in the range from 1:0.5 to 1:6.0 and preferably in the range from 1:1 to 1:3.0. The process shows particular advantages in regard to selectivity where about 2 moles of ethylene oxide are reacted per mole of dicarboxylic acid (molar ratio 2:1).

The ethoxylation may be carried out at temperatures of 90° C. to 130° C., but is preferably carried out at a temperature of 100 to 120° C. If reaction temperatures above 140° C. are selected for the process as a whole, the selectivity of the-addition of ethylene oxide diminishes. Autogenous pressures of 1 to 5 bar and preferably 3 to 5 bar are recommended for the ethoxylation reaction. At the end of the reaction, it is advisable to stir the reaction mixture for a certain time (15 to 90 mins.) at the reaction temperature and under the autogenous pressures in order to complete the reaction. The autoclave is then cooled, vented and, if desired, acids such as, for example, lactic acid or phosphoric acid are added to the product in order to neutralize the basic catalyst.

The foregoing observations on the pure ethoxylation reaction also apply accordingly to the pure propoxylation and to the mixed ethoxylation and propoxylation reaction. For the mixed ethoxylation and propoxylation reaction, either a mixture of ethylene oxide and propylene oxide or first ethylene oxide and then propylene oxide or vice versa may be reacted with the unbranched aliphatic dicarboxylic acids, the molar ratios of unbranched aliphatic dicarboxylic acids to alkylene oxide, i.e. ethylene oxide and propylene oxide in the mixed ethoxylation and propoxylation reaction, being in the above-mentioned range of 1:0.5 to 1:6, preferably in the range from 1:1 to 1:3 and more preferably of the order of 1:2.

In principle, the process according to the invention is also suitable for alkoxylation with butylene oxide, although the alkoxylation reaction is preferably carried out with ethylene oxide and/or propylene oxide and, more particularly, with ethylene oxide only.

The addition of the alkylene oxides onto the two carboxyl groups of the dicarboxylic acid is a statistical process, i.e. alkylene oxide units are added onto both carboxyl groups with a very high degree of probability.

The process according to the invention gives product mixtures, alkylene glycol monoesters of the branched aliphatic dicarboxylic acids which correspond to formula (II):

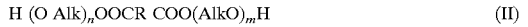

in which R is as defined for formula (I), Alk is an alkylene oxide unit, more particularly a $CH_2CH_2$, $CHCH_3CH_2$ and/or $CH_2CHCH_3$ unit, and n and m are each a number of 0 to 6.0, the sum of n+m being a number of 0.5 to 6, being formed in quantities of preferably more than 85% by weight and, more preferably, more than 90% by weight. In one particular embodiment, n and m in formula (II) stand for the number 1.

As can be seen from formula (II), by far the majority of the product mixtures obtained in accordance with the invention are monoesters of alkylene glycols, i.e. the alkylene glycols added on still have one free hydroxyl group and are esterified at the other hydroxyl group with a carboxyl group of the unbranched aliphatic dicarboxylic acid. If the free hydroxyl group of the alkylene glycols is esterified with another carboxyl group of another unbranched aliphatic dicarboxylic acid, higher molecular diesters of alkylene glycols are formed. Another advantage of the process according to the invention is that the percentage content of such diesters, which is particularly problematical in the case of the higher molecular unbranched aliphatic dicarboxylic acids, can be reduced. Thus, the products obtained by the process according to the invention preferably have a monoester content of more than 85% by weight and, in particular, more than 90% by weight and a diester content below 7% by weight and preferably below 5% by weight, based on the end product. The balance to 100% by weight consists of unreacted residual acid.

The selectivity of the process according to the invention is reflected in the fact that at least 90% by weight and preferably at least 95% by weight of the compounds corresponding to formula (II) have substantially the same number as the degree of alkoxylation n or m, the sum of n and m corresponding to the reaction ratios of alkylene oxide per mole of unbranched aliphatic dicarboxylic acid. In other words, compounds of formula (II) of which at least 90% have substantially the same value (i.e. 1) for n and m are formed in the addition of 2 moles of ethylene oxide onto 1 mole of unbranched aliphatic dicarboxylic acids.

The addition products obtained by the process according to the invention may be regarded in the broadest sense as diols with an ester function which may be used, for example, in the production of polyesters. Accordingly, the present invention also relates to the use of the addition products of alkylene oxides with unbranched aliphatic dicarboxylic acids produced in accordance with claim 1 as a monomer unit for polymers, more particularly for polyesters.

EXAMPLES

Example 1

658.5 g (3.5 moles) of azelaic acid were introduced into an autoclave, followed by the addition of 7.3 g of triethanolamine (corresponding to 1.2% by weight, based on dicarboxylic acid). The autoclave was then alternately evacuated for 30 minutes at 80° C./30 mbar and purged with nitrogen a total of three times in order to remove traces of water which could lead to the formation of polyethylene glycol. After the reaction mixture had been purged with nitrogen for the last time, the autoclave was closed and heated to 100° C. and 308 g (7 moles) of ethylene oxide were introduced in portions at a maximum pressure of 5 bar. On completion of the reaction, which was reflected in the fact that the pressure fell back to 1.2 bar and then remained constant, the reaction mixture was stirred for 60 minutes at 100° C./5 bar and was then cooled and vented. The basic catalyst remained in the end product.

The product obtained had a monoester content with 1 mole of ethylene oxide per carboxyl group of 91.3% by weight, a monoester content with more than 1 mole of ethylene oxide per carboxyl group of 2.6% by weight, an ethylene glycol diester content of 3.0% by weight and a residual acid content of 3.1% by weight.

The composition of the product shows that, on the one hand, the process according to the invention produces monoesters in high yields and that, on the other hand, the process according to the invention is highly selective because the predominant quantity of the monoesters are compounds which contain only 1 mole of ethylene oxide per mole of carboxyl group of the unbranched aliphatic dicarboxylic acid, as required on the basis of the quantities of ethylene oxide used.

What is claimed is:

1. A process for producing alkylene glycol esters of unbranched aliphatic dicarboxylic acids, said process comprising reacting an alkylene oxide and an unbranched aliphatic dicarboxylic acid in the presence of a basic catalyst to produce an alkylene glycol ester product, wherein said basic catalyst comprises an alkanolamine, and wherein said alkylene glycol ester product has a monoester content greater than 85% by weight.

2. The process according to claim 1, wherein said unbranched aliphatic dicarboxylic acid is an $\alpha,\omega$-dicarboxylic acid selected from the group consisting of malonic acid, succinic acid, adipic acid and azelaic acid.

3. The process according to claim 1, wherein said alkylene oxide is selected from the group consisting of ethylene oxide, propylene oxide and mixtures thereof.

4. The process according to claim 1, wherein said alkylene oxide comprises ethylene oxide.

5. The process according to claim 1, wherein said unbranched aliphatic dicarboxylic acid and said alkylene oxide are present in a mole ratio of from about 1:0.5 to about 1:6.

6. The process according to claim 1, wherein said unbranched aliphatic dicarboxylic acid and said alkylene oxide are present in a mole ratio of from about 1:1 to about 1:3.

7. The process according to claim 1, wherein said alkanolamine comprises triethanolamine.

8. The process according to claim 1, wherein said alkanolamine is present in an amount of from about 0.05% to 5% by weight based upon the total weight of said dicarboxylic acid.

9. The process according to claim 1, wherein the reaction of said alkylene oxide and said dicarboxylic acid is carried out at a temperature of from about 90° C. to about 130° C.

10. The process according to claim 1, wherein the reaction of said alkylene oxide and said dicarboxylic acid is carried out at an autogenous pressure of from about 1 bar to about 5 bars.

11. The process according to claim 1, wherein the reaction of said alkylene oxide and said dicarboxylic acid is carried out at an autogenous pressure of from about 3 bars to about 5 bars.

* * * * *